(12) United States Patent
Edwards

(10) Patent No.: US 7,087,819 B2
(45) Date of Patent: Aug. 8, 2006

(54) NON-PUNGENT ORNAMENTAL PEPPERS

(76) Inventor: Marlin Edwards, 1445 Bald Eagle Rd., Wildwood, MO (US) 63038

( * ) Notice: Subject to any disclaimer, the term of this patent is extended or adjusted under 35 U.S.C. 154(b) by 0 days.

(21) Appl. No.: 09/564,153

(22) Filed: May 3, 2000

(65) Prior Publication Data

US 2003/0097674 A1    May 22, 2003

Related U.S. Application Data

(60) Provisional application No. 60/132,389, filed on May 4, 1999.

(51) Int. Cl.
- *A01H 1/00* (2006.01)
- *A01H 4/00* (2006.01)
- *A01H 5/00* (2006.01)
- *A01H 5/10* (2006.01)

(52) U.S. Cl. .................. 800/317.1; 800/298; 800/260; 435/410

(58) Field of Classification Search ............. 800/317.1, 800/260, 266; 435/410
See application file for complete search history.

(56) References Cited

U.S. PATENT DOCUMENTS

| | | | | |
|---|---|---|---|---|
| 5,304,719 A | * | 4/1994 | Segebart | ...................... 800/303 |
| 5,367,109 A | * | 11/1994 | Segebart | ................... 800/320.1 |
| 5,811,640 A | * | 9/1998 | Grun et al. | |
| 5,850,009 A | * | 12/1998 | Kevern | ........................ 800/271 |
| 5,959,186 A | * | 9/1999 | Arevalos et al. | |

OTHER PUBLICATIONS

Harvell et al, The Environment Produces a Signfifcant Effect on Pungency of Chiles, 1997, HortSceince, vol. 32, No. 7, p. 1292.*

Barbara Pickersgill, Genetic Resources and Breeding of Capsicum Spp., 1997, Euphytica, vol. 96, pp. 129-133.*
Jean Andrews, Peppers, the Domesticated Capsicums, 1984, Library of Congress, p. 83.*
Thompson and Morgan Inc. Spring 1991 Catalog, P.O. Box 1308, Jackson, New Jersey 08527, p. 63.*
Plant Variety Certificate 200000140 for Medusa filed Jan. 21, 2000.
Dave DeWitt, *The Chile Pepper Encyclopedia*, William Morrow and Company, Inc. p. 217-218 (1999).
Dave DeWitt & Paul W. Bosland, *Peppers of the World*, Ten Speed Press, p. 96, 102, 105, 106, 107, 108, 109, 110, 111, 113, 117 (1996).
Dave DeWitt and Nancy Gerlach, *The Whole Chile Pepper Book*, Little, Brown and Company, p. 30-31 (1990).
Miller et al., *American Society for Horticultural Science*, 544-550 (date unknown).
Eshbaugh et al., *Bulletin of the Torrey Botanical Club* 102(6):396-403 (1976).
Deshapnde, *Indian Journal of Agricultural Science*, 5:513-516 (1935).
Cooper, et al., *J. Agric. Food Chem*. 39:2253-2256 (1991).
Lippert, et al., *The Botanical Review*, 32:24-55 (1966).
"Capsicum" *Hortus Third A Concise Dictionary of Plants Cultivated in the United States and Canada*, MacMillan Publishing Company 1976, p. 219.

* cited by examiner

*Primary Examiner*—David H Kruse
(74) *Attorney, Agent, or Firm*—Wood, Phillips, Katz, Clark & Mortimer

(57) ABSTRACT

The present invention relates to new, distinct and stable non-pungent ornamental pepper cultivars. The ornamental pepper cultivars of the present invention contain a gene complex which confers non-pungency and ornamental phenotypes to the pepper plant.

21 Claims, 6 Drawing Sheets

NON-PUNGENT ORNAMENTAL PEPPERS

RELATED APPLICATION INFORMATION

This application claims priority from U.S. Application No. 60/132,389 filed on May 4, 1999.

FIELD OF THE INVENTION

The present invention relates to a novel gene complex which confers non-pungency and ornamental phenotypes in pepper cultivars of the genus *Capsicum*.

This invention also relates to ornamental pepper seed, an ornamental pepper plant, ornamental pepper variety and an ornamental pepper hybrid which contain this gene complex. In addition, the present invention also relates to methods for transferring this gene complex from sweet pepper to ornamental pepper varieties and species and is useful for producing novel types and varieties of ornamental peppers which exhibit the non-pungency phenotype.

BACKGROUND OF THE INVENTION

Within the genus *Capsicum*, several cultivars possess an aesthetic value for ornamental purposes in the garden and as indoor pot plants. Ornamental peppers can provide a range of pod shapes and colors complemented by varying degrees of green or purple foliage. Classification of ornamental peppers includes cultivars within three species: *Capsicum annuum* L., *Capsicum chinense* Jacq., and *Capsicum pendulum* Willd. (See, Corley, W. L. and A. H. Dempsey. 1972. *Ornamental Pepper Evaluation* 1965–1971. University of Georgia College of Agriculture Experiment Stations Research Report 136:10 pp.).

Fruits of the ornamental peppers are edible but very pungent (See, Corley, W. L. and A. H. Dempsey, *Ornamental Pepper Evaluation* 1965–1971. University of Georgia College of Agriculture Experiment Stations Research Report 136:10 pp. (1972)). The pungent active ingredient found in peppers is the aromatic phenol capsaicin, which is capable of causing severe irritation. Capsaicin is produced by oil secreting glands located along the placenta. The presence or absence of pungency in *Capsicum* is reported to have simple trait inheritance with pungency partially dominant to non-pungency (See, Deshpande, R. B., *Indian Journal of Agricultural Science*, 5:513–516 (1935). The degree of pungency within a genotype is subject to unidentified genetic factors and the environment, in particular temperature. (See, Lippert, L. F., et al., *The Botanical Review*, 32:24–55 (1966)).

Non-pungency is a characteristic of the Grossum Group of *Capsicum annuum* L. Var. *annuum*, containing the commonly known peppers Bell Pepper, Sweet Pepper or Green Pepper. (*Hortus Third A Concise Dictionary of Plants Cultivated in the United States and Canada*, MacMillan Publishing Company 1976) It would be desirable to have non-pungent ornamental peppers thereby eliminating possible hazards from capsaicin in the landscape or indoor environment.

SUMMARY OF THE PRESENT INVENTION

The present invention relates to a non-pungent ornamental pepper plant which produces peppers having capsaicin levels which are statistically equal to or less than the capsaicin levels of peppers from a commercial sweet green pepper cultivar at the $\alpha=0.05$ confidence level. The ornamental pepper plants of the present invention contain a gene complex which confers non-pungency and ornamental phenotypes and has the pedigrees 96P601, 96P631, 96P610 and 97P1938. The present invention also relates to seed, pollen, cuttings, and ovules of the non-pungent ornamental pepper plants of the present invention. Moreover, the present invention also relates to a tissue culture comprising regenerable cells of the non-pungent ornamental pepper plant of the present invention.

Additionally, the present invention relates to ornamental pepper seed containing a gene complex which confers non-pungency and ornamental phenotypes to ornamental pepper plants grown from this seed. The seed of the present invention has pedigrees which include 96P601, 96P631, 96P610 and 97P1938. The present invention also relates to a non-pungent ornamental pepper plant produced by growing seed of the present invention.

Also, the present invention relates to non-pungent ornamental peppers having capsaicin levels which are statistically equal to or less than the capsaicin levels of peppers from commercial sweet green pepper cultivars at the $\alpha=0.05$ confidence level. The ornamental peppers of the present invention contain a gene complex which confers non-pungency and ornamental phenotypes.

The present invention also relates to a method for transferring a non-pungency gene from sweet pepper plants to ornamental pepper plants. The method involves the steps of crossing a non-pungent sweet pepper plant containing a gene for non-pungency with a pungent ornamental pepper plant. Seeds resulting from this cross are then collected and regenerated into plants. Pepper plants containing a gene complex conferring non-pungency and an ornamental phenotype are selected from the regenerated plants. The method also involves crossing the selected non-pungent ornamental peppers containing this gene complex which confers non-pungency and ornamental attributes with other non-pungent ornamental peppers containing a gene complex which confers non-pungency and ornamental attributes or with pungent ornamental pepper plants having commercially desirable phenotypic traits for a sufficient number of generations to obtain a non-pungent ornamental pepper plant containing the gene complex which confers non-pungency and a desirable ornamental phenotype.

Finally, the present invention relates to viable non-pungent ornamental pepper seeds and plants and succeeding generations thereof which are grown from seeds deposited under ATCC Accession Number 203779 and to ornamental pepper seeds and plants to which the gene complex which confers non-pungency and ornamental phenotypes is transferred from the deposited seeds in succeeding generations thereof.

DETAILED DESCRIPTION OF THE INVENTION

Figure 1:
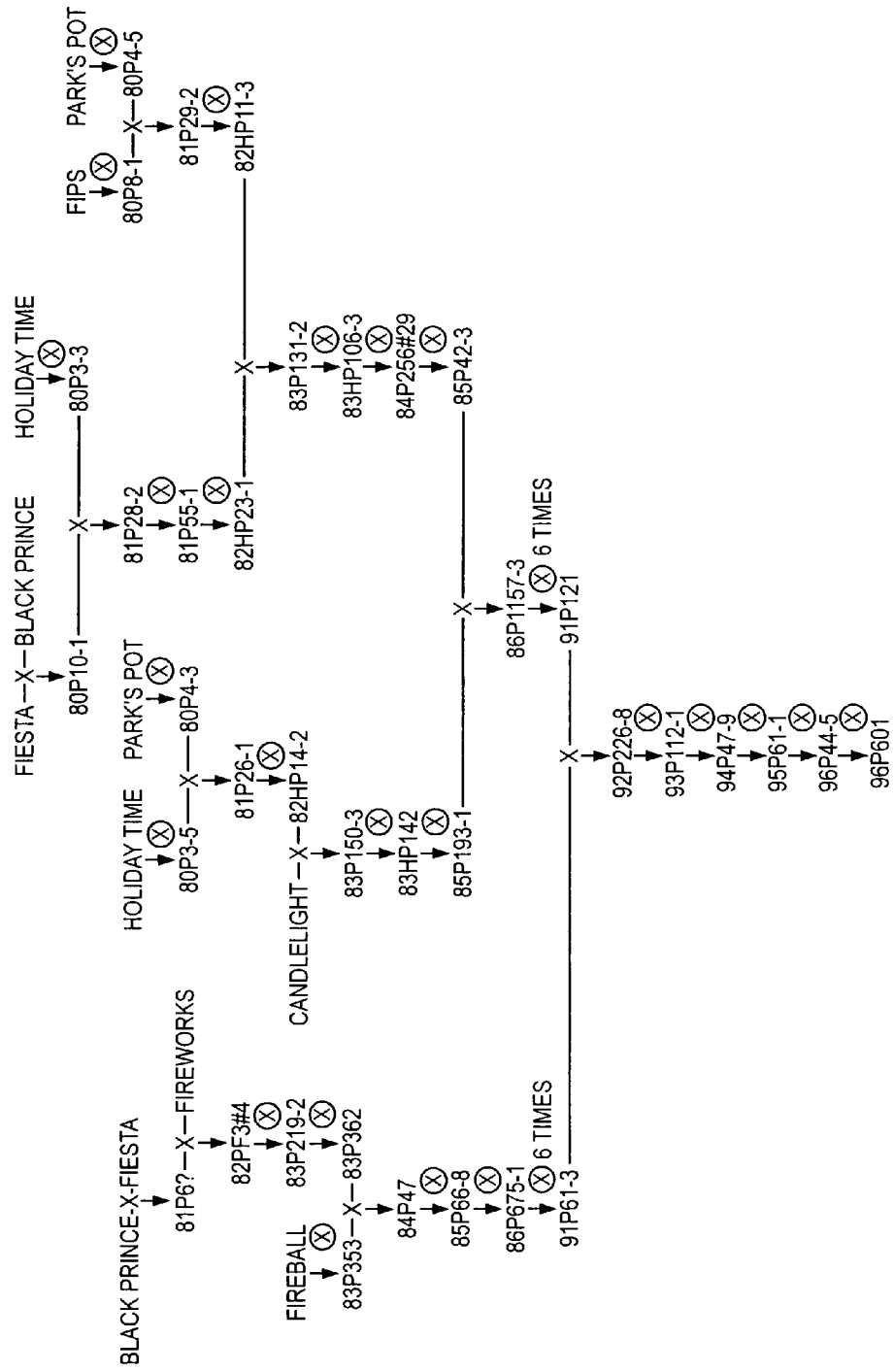
FIG. 1 shows the pedigree of non-pungent ornamental pepper cultivar 96P601.

The ornamental pepper cultivars of the present invention produce fruit (peppers) which have capsaicin levels which are statistically equal to or less than the capsaicin levels of peppers from a commercial sweet green pepper cultivar at the $\alpha=0.05$ confidence level. A transferrable gene complex, which results in the peppers of the present invention having no pungency and ornamental phenotypes, has been discovered and incorporated into other genetic backgrounds.

As used herein, the term "non-pungency" refers to a capsaicin level as measured in Scoville Heat Units. Non-pungent ornamental peppers are characterized as having capsaicin levels which are statistically equal to or less than the capsaicin levels of peppers from a commercial sweet green pepper cultivar at the $\alpha=0.05$ confidence level. Sweet green peppers, while not produced for the ornamental market, can be used as a non-pungent benchmark based on their classification in the non-pungent *Capsicum grossum* Group (See *Hortus Third A Concise Dictionary of Plants Cultivated in the United States and Canada*, MacMillan Publishing Company 1976, herein incorporated by reference).

As used herein, the term "ornamental pepper" means a pepper plant possessing ornamental characteristics, including fruit number, fruit weight, height, branching, leaf length and leaf width, that are not statistically less desirable than those of commercially available pungent ornamental peppers. Examples of pungent ornamental peppers include 'Red Missile', 'Holiday Flame' and 'Masquerade' all available from Ball Horticultural Company, 622 Town Road, West Chicago, Ill., 60185.

As used herein, the germ "gene complex" means a gene(s) or allele(s) which confer non-pungency and ornamental phenotypes when transferred into a plant which does not contain said gene(s) or allele(s). The gene complex described herein may be transferred into a plant which does not contain the gene complex using traditional breeding techniques or by genetic engineering. Specifically, one or more genes comprising the gene complex can be inserted in the antisense direction in an expression construct using techniques well-known in the art, in order to "knock-out" capsaicin production.

The ornamental pepper cultivars of the present invention are genetically stable. Additionally, the gene complex described herein which conveys non-pungency and ornamental phenotypes can be bred into diverse ornamental pepper backgrounds.

As previously discussed, the non-pungent ornamental peppers of the present invention are genetically stable, as evidenced by the stability of the trait through sexual crosses. Depending upon the cultivar, however, the degree of pungency per fruit or plant may be adversely affected by environmental stress factors, without any variance in the genotype of the plant. Environmental stress factors which may adversely affect the degree of pungency per fruit include, but are not limited to, high temperatures, low soil fertility, or water stress.

The non-pungent ornamental pepper cultivars of the present invention maintain functional male and female organs, thus making the incorporation of the ornamental phenotypes with non-pungency trait into other ornamental pepper cultivars possible. Non-pungency may be incorporated into cultivars with a range of pod shapes and colors complemented by varying degrees of green or purple foliage.

It is expected that non-pungency can be predictably transferred into any ornamental pepper background using the methods described herein. Recurrent selection for progeny having non-pungency and ornamental pepper characteristics can be bred into diverse ornamental pepper backgrounds. Intermating of superior genotypes which exhibit non-pungency and ornamental characteristics through repeated generations has resulted in the selection of cultivars with non-pungency and improved ornamental characteristics. Periodic outcrossing is done during the breeding program in order to introduce desirable characteristics and to circumvent inbreeding depression.

It is expected that any selected non-pungent ornamental pepper cultivar can be produced as progeny from sexual crosses and sold as seed. Methods for the storage of such seed is well known in the art.

The present invention also relates to a method of transferring a gene for non-pungency from a sweet pepper plant to a pungent ornamental pepper plant. The method involves the steps of crossing a sweet pepper plant containing a gene for non-pungency with a pungent ornamental pepper plant. The seeds resulting from the cross are collected, planted and regenerated into plants. Non-pungent ornamental pepper plants which contain the gene complex which confers non-pungency and ornamental attributes are then selected from the regenerated plants. In addition, the method further involves crossing the selected non-pungent ornamental pepper plants containing the gene complex which confers non-pungency and ornamental attributes with other non-pungent ornamental pepper plants containing the gene complex which confers non-pungency and ornamental attributes or with pungent ornamental pepper plants having commercially desirable phenotypic traits for a sufficient number of generations, to obtain non-pungent ornamental pepper plants containing the gene complex which confers non-pungency and desirable ornamental phenotype.

This previously unknown non-pungent ornamental pepper characteristic arose from breeding and research efforts. The non-pungency gene originated from two sweet green pepper sources, which are identified as 'Park's Pot' and 'California Wonder'. 'Park's Pot' is a bell pepper cultivar that was intended for pot plant culture and has large, bell-shaped fruit and is commercially available from Geo. W. Park Seed Co. Inc., 1 Parkton Avenue, Greenwood, S.C., 29647. 'California Wonder' has large, green, pendent, sweet, three to four lobed, bell-shaped peppers and is commercially available from The Pepper Gal, P.O. Box 23006, Fort Lauderdale, Fla. 33311.

By way of example, and not of limitation, examples of the present invention will now be given.

EXAMPLE 1

Pedigree for Non-Pungent Ornamental Pepper Cultivar 96P601

FIG. 1 shows the pedigree for non-pungent ornamental pepper cultivar 96P631

EXAMPLE 2

Pedigree for Non-Pungent Ornamental Pepper Cultivar 96P631

Figure 2:
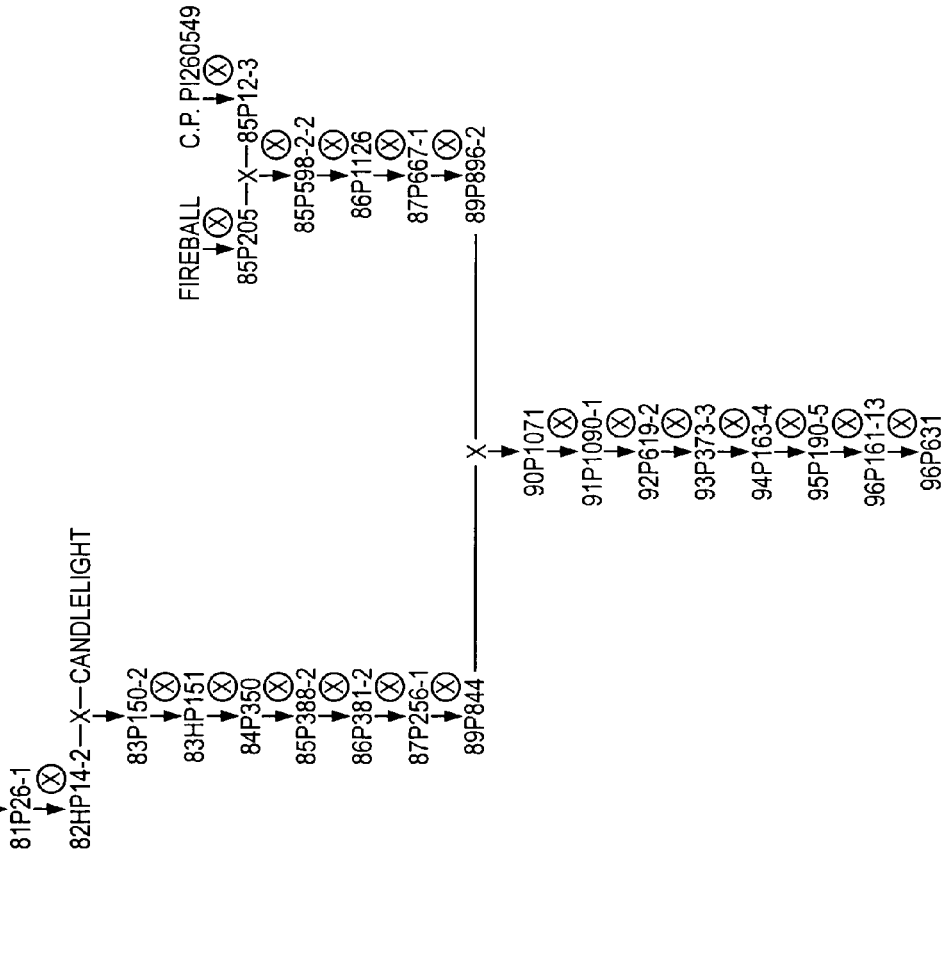
FIG. 2 shows the pedigree of non-pungent ornamental pepper cultivar 96P631.

FIG. 2 shows the pedigree for non-pungent ornamental pepper cultivar 96P631.

EXAMPLE 3

Pedigree for Non-Pungent Ornamental Pepper Cultivar 97P1938

Figure 3:
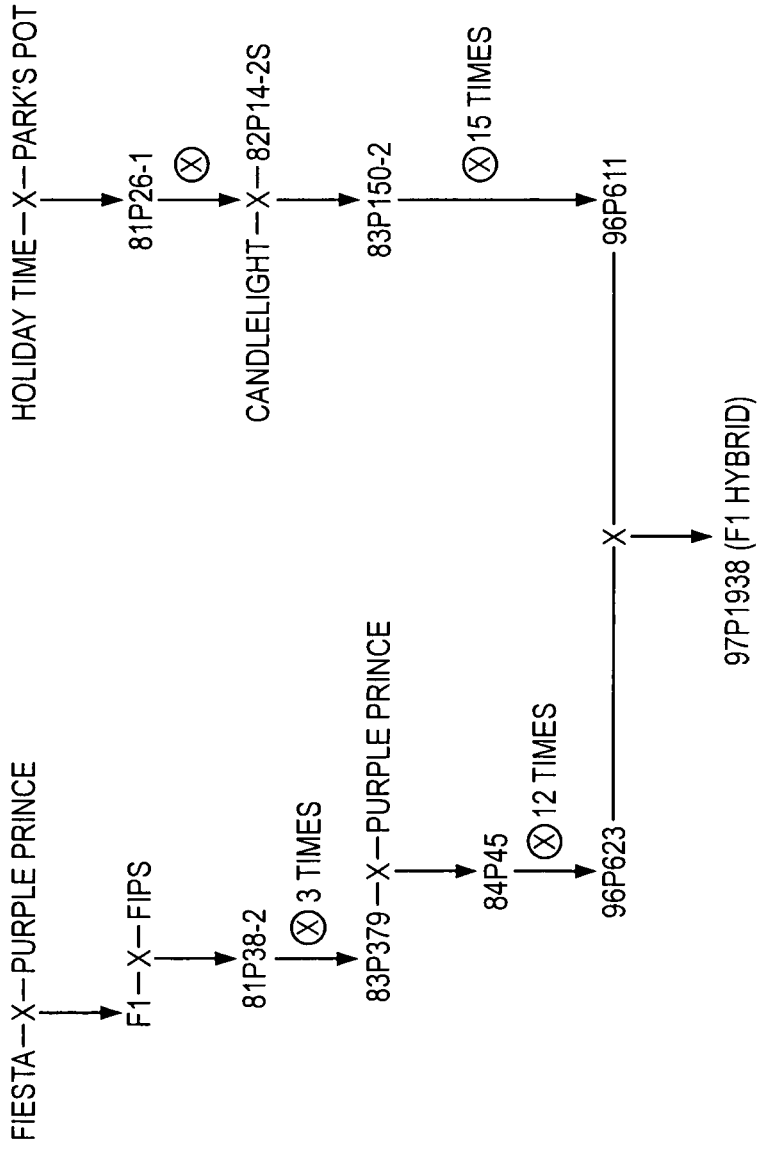
FIG. 3 shows the pedigree of non-pungent ornamental pepper cultivar 97P1938.

FIG. 3 shows the pedigree for non-pungent ornamental pepper cultivar 97P1938.

EXAMPLE 4

Evaluation of Capsaicin in Ornamental Pepper Cultivars

To evaluate the degree of pungency, capsaicin levels, as measured in Scoville Heat Units, were determined. For capsaicin analysis, fruit from ten pepper varieties were collected from greenhouse-grown material, and a commercial Sweet Green pepper was purchased locally. Plants were grown in a 1999 trial at Pan American Seed Company located in Elburn, Ill.

Included in the analysis were non-pungent ornamental peppers of the present invention: 96P601, 96P610, 96P631 and 97P1938. Selection 96P611 is a parent of the hybrid pepper 97P1938. The varieties 'Red Missile', 'Masquerade' and 'Holiday Flame' were used as commercial ornamental pepper controls. Also evaluated was 'Triton', which is a non-pungent pepper marketed by Ball Horticultural Company, and A PI 'Sweet Orange' which was referred to in a publication as being a non-pungent ornamental pepper with "good ornamental characteristics" (See, Corley, W. L. and A. H. Dempsey, Ornamental Pepper Evaluation 1965–1971. University of Georgia College Agriculture Experiment Stations Research Report 136: 10 pp. (1972)).

For analysis, pepper fruit were dried at 40° C. Three whole pepper fruits from three separate plants of each variety were ground into a fine powder and 200 mg was weighed and collected in a 5 ml tube. Two mls of methanol were added and mixed for 1 minute using a Prohomogenizer. The mixture was centrifuged and the supernatant passed through a 0.2 um filter. Capsaicin levels were measured using HPLC. Samples of 50 ul were injected into a Supelcosil LC-18 25 cm×4.6 mm column and run at 1.5 ml/minute for 26 minutes using 60/40, methanol/water. Conditions and separation techniques followed the method of T. Cooper et al., *J. Agric. Food Chem.*, 39, 2253–2256 (1991). The results are shown below in Table 1.

TABLE 1

| Variety | Average Scoville Heat Units | Tukey Grouping ($\alpha = 0.05$) |
|---|---|---|
| Sweet Green pepper | 96.8 | C |
| 'Red Missile' | 19708.3 | AB |
| 'Masquerade' | 36799.2 | A |
| 'Holiday Flame' | 34043.4 | A |
| 96P601 | 175.4 | C |
| 96P610 | 128.1 | C |
| 96P631 | 191.9 | C |
| 97P1938 | 121.9 | C |
| 96P611 | 137.9 | C |
| 'Triton' | 113.8 | C |
| 'Sweet Orange' | 5768.4 | B |

Analysis was completed using Tukey's Studentized Range Test and logarithmic transformed values of the original data. Analysis identifies no significant difference between the Sweet Green pepper, 96P601, 96P610, 96P631, 97P1938, 96P611 or 'Triton'. The PI 'Sweet Orange' had a significantly higher capsaicin level than the ornamental peppers of the present invention, indicating that 'Sweet Orange' should not be classified as being non-pungent. The capsaicin levels of all non-pungent selections tested were significantly lower than the pungent ornamental controls 'Red Missile', 'Masquerade' and 'Holiday Flame'.

EXAMPLE 5

Comparison of Ornamental Characteristics of Non-Pungent and Pungent Peppers

Six greenhouse plants of each cultivar listed in Table 2, below, were evaluated for fruit number, fruit weight, height, lateral branches, leaf length and leaf width. For fruit weight, five fruit from each of six plants were individually weighed and an average weight per plant was analyzed. For leaf length and leaf width, five mature basal leaves were measured and an average measurement per plant was analyzed. The three commercial pungent cultivars 'Red Missile', 'Holiday Flame' and 'Masquerade' were randomly selected. Plants were grown in a 1999 trial at PanAmerican Seed Company located in Elburn, Ill. Means were compared using the Least Significant Difference Test ($\alpha = 0.05$). All non-pungent cultivars of the present invention possess ornamental characteristics that are statistically equivalent or superior to the commercial pungent ornamental peppers. In contrast, 'Triton' a non-pungent pepper marketed by Ball Horticultural Company, does not possess the desirable phenotype of the commercial pungent ornamental peppers. It has significantly less and larger fruit, it is significantly less branched, and has significantly longer and wider leaves than the commercial pungent ornamental peppers. A PI 'Sweet Orange' was referred to in a publication as being a non-pungent ornamental pepper which had "good ornamental characteristics" (See, Corley, W. L. and A. H. Dempsey, Ornamental Pepper Evaluation 1965–1971. University of Georgia College of Agriculture Experiment Stations Research Report 136: 10 pp. (1972)). The ornamental characteristics of 'Sweet Orange' are statistically less desirable than commercial pungent ornamental peppers for all characteristics evaluated.

TABLE 2

| Variety | Fruit Number | 5% LSD LSD = 9.4 | Fruit Weight (g) | 5% LSD LSD = 1.5 | Plant Height (cm) | 5% LSD LSD = 2.8 | Lateral Branches | 5% LSD LSD = 1.2 |
|---|---|---|---|---|---|---|---|---|
| 'Red Missile' | 51.7 +/− 4.9 | bc | 0.9 +/− 0.2 | a | 18.6 +/− 1.7 | b | 9.3 +/− 1.2 | e |
| 'Masquerade' | 63.5 +/− 7.5 | d | 1.9 +/− 0.1 | a | 29.3 +/− 2.8 | d | 7.3 +/− 1.5 | c |
| 'Holiday Fame' | 55.8 +/− 10.3 | cd | 1.8 +/− 0.3 | a | 18.7 +/− 2.7 | b | 7.3 +/− 1.0 | c |

TABLE 2-continued

| | | | | | | | | |
|---|---|---|---|---|---|---|---|---|
| 96P601 | 44.5 +/− 4.3 | b | 1.1 +/− 0.1 | a | 9.8 +/− 0.5 | a | 7.7 +/− 0.5 | cd |
| 96P610 | 59.5 +/− 2.7 | cd | 0.8 +/− 0.1 | a | 8.9 +/− 0.9 | a | 9.5 +/− 1.2 | e |
| 96P631 | 83.2 +/− 15.1 | e | 0.9 +/− 0.1 | a | 1.9 +/− 1.3 | b | 8.8 +/− 0.8 | de |
| 97P1938 | 95.2 +/− 12.3 | ef | 1.1 +/− 0.1 | a | 2.6 +/− 2.8 | c | 11.8 +/− 1.2 | f |
| 'Triton' | 7.8 +/− 1.5 | a | 14.1 +/− 2.5 | c | 18.5 +/− 2.2 | b | 2.3 +/− 0.5 | a |
| 'Sweet Orange' | 10.5 +/− 5.7 | a | 10.6 +/− 3.0 | b | 35.5 +/− 4.6 | e | 3.7 +/− 0.8 | b |

| Variety | Leaf Length (cm) | 5% LSD LSD = 0.7 | Leaf Width (cm) | 5% LSD LSD = 0.4 |
|---|---|---|---|---|
| 'Red Missile' | 8.2 +/− 0.4 | d | 4.0 +/− 0.2 | c |
| 'Masquerade' | 7.1 +/− 0.2 | bc | 3.3 +/− 0.1 | b |
| 'Holiday Fame' | 7.6 +/− 0.6 | cd | 3.2 +/− 0.2 | b |
| 96P601 | 5.8 +/− 0.3 | a | 2.3 +/− 0.1 | a |
| 96P610 | 6.1 +/− 0.1 | a | 2.6 +/− 0.2 | a |
| 96P631 | 5.5 +/− 0.3 | a | 2.4 +/− 0.1 | a |
| 97P1938 | 7.0 +/− 0.4 | bc | 3.2 +/− 0.2 | b |
| 'Triton' | 11.4 +/− 1.1 | e | 5.8 +/− 0.4 | e |
| 'Sweet Orange' | 11.0 +/− 1.3 | e | 4.9 +/− 0.7 | d |

EXAMPLE 6

Comparison of 'Sweet Pickle' and 96P611 Ornamental Characteristics

Figure 4:
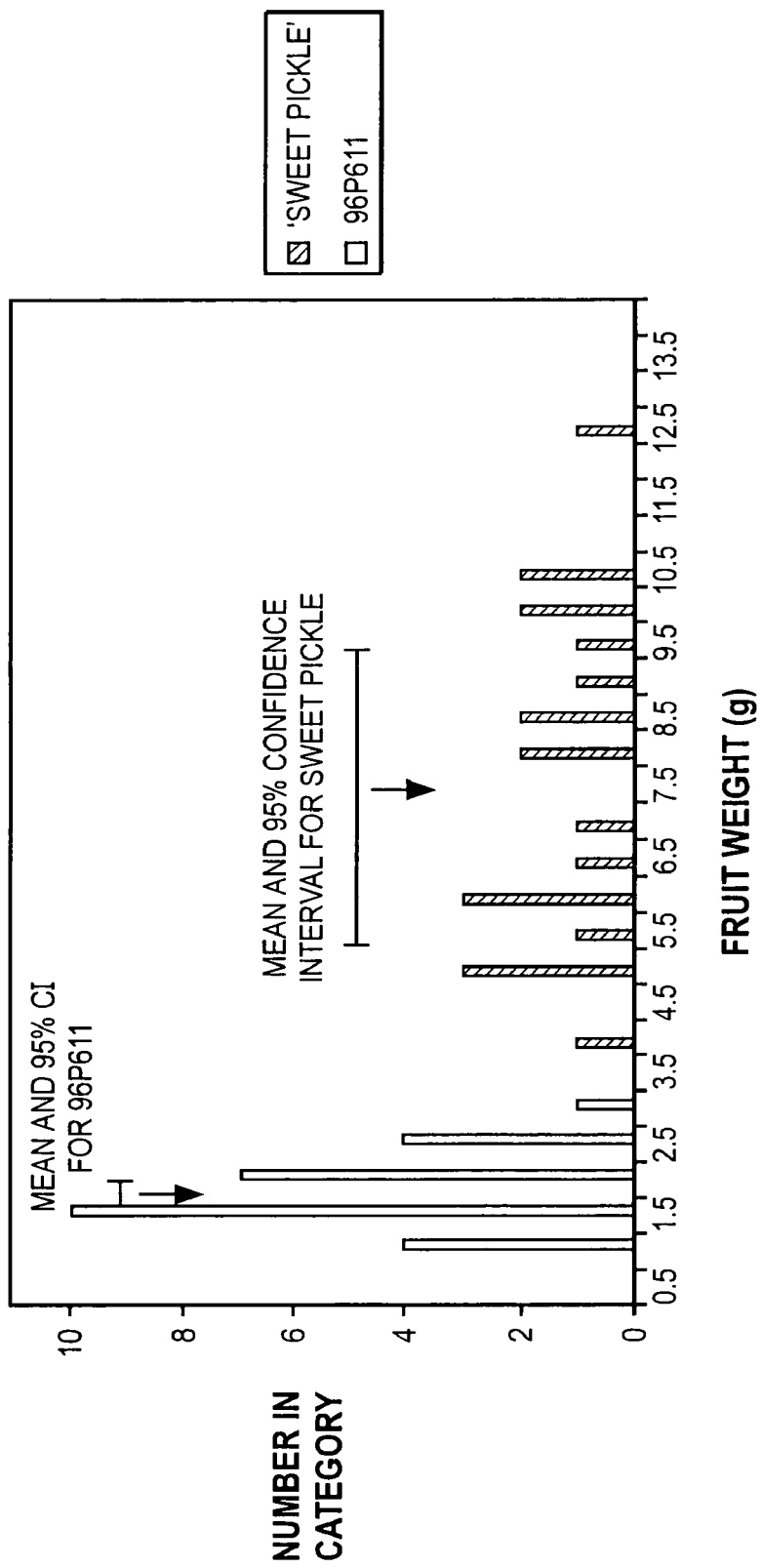
FIG. 4 shows a comparison of the fruit weights of 'Sweet Pickle' and cultivar 96P611 of the present invention.
Figure 5:
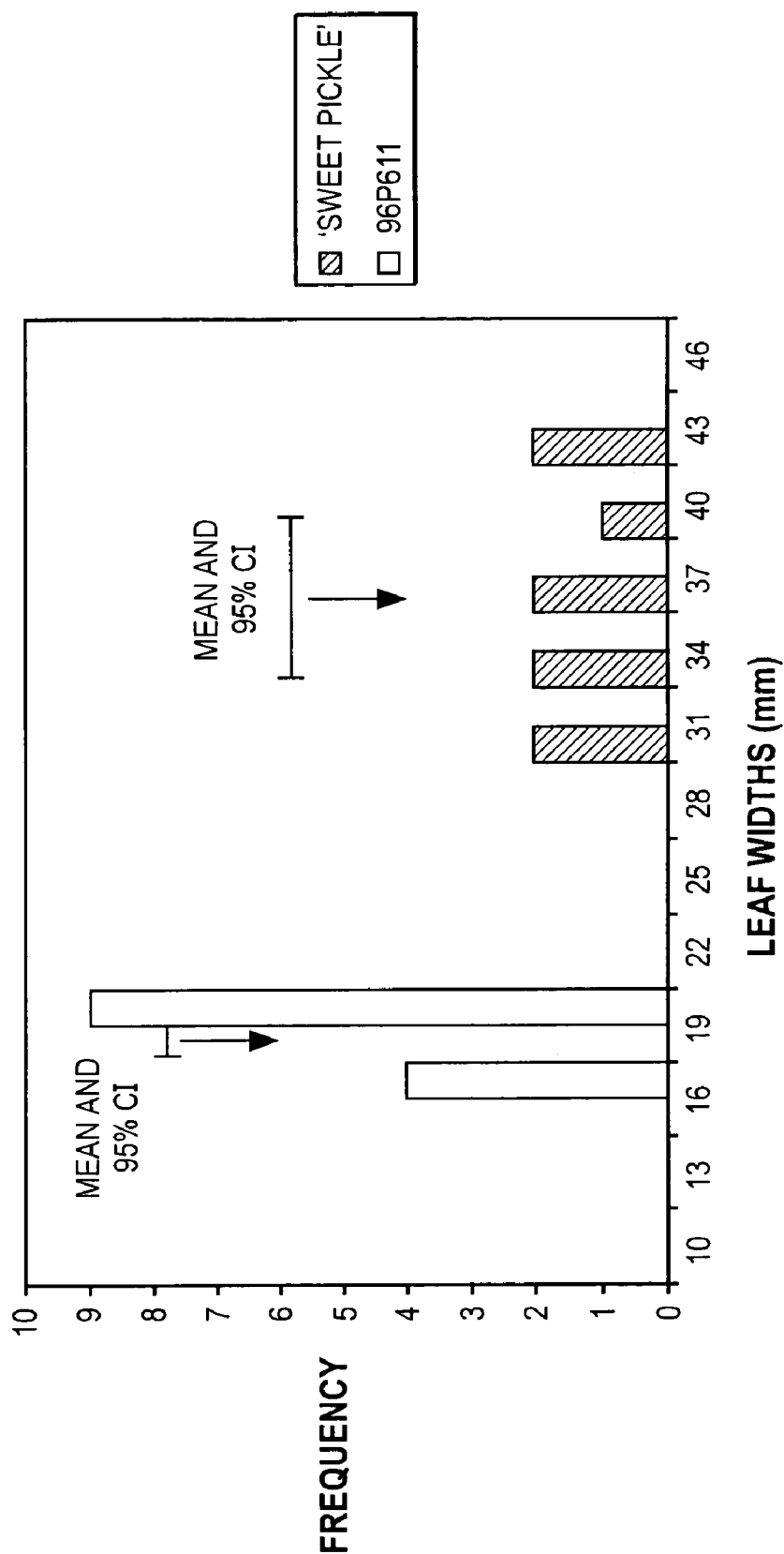
FIG. 5 shows a comparison of the leaf widths of 'Sweet Pickle' and cultivar 96P611 of the present invention.
Figure 6:
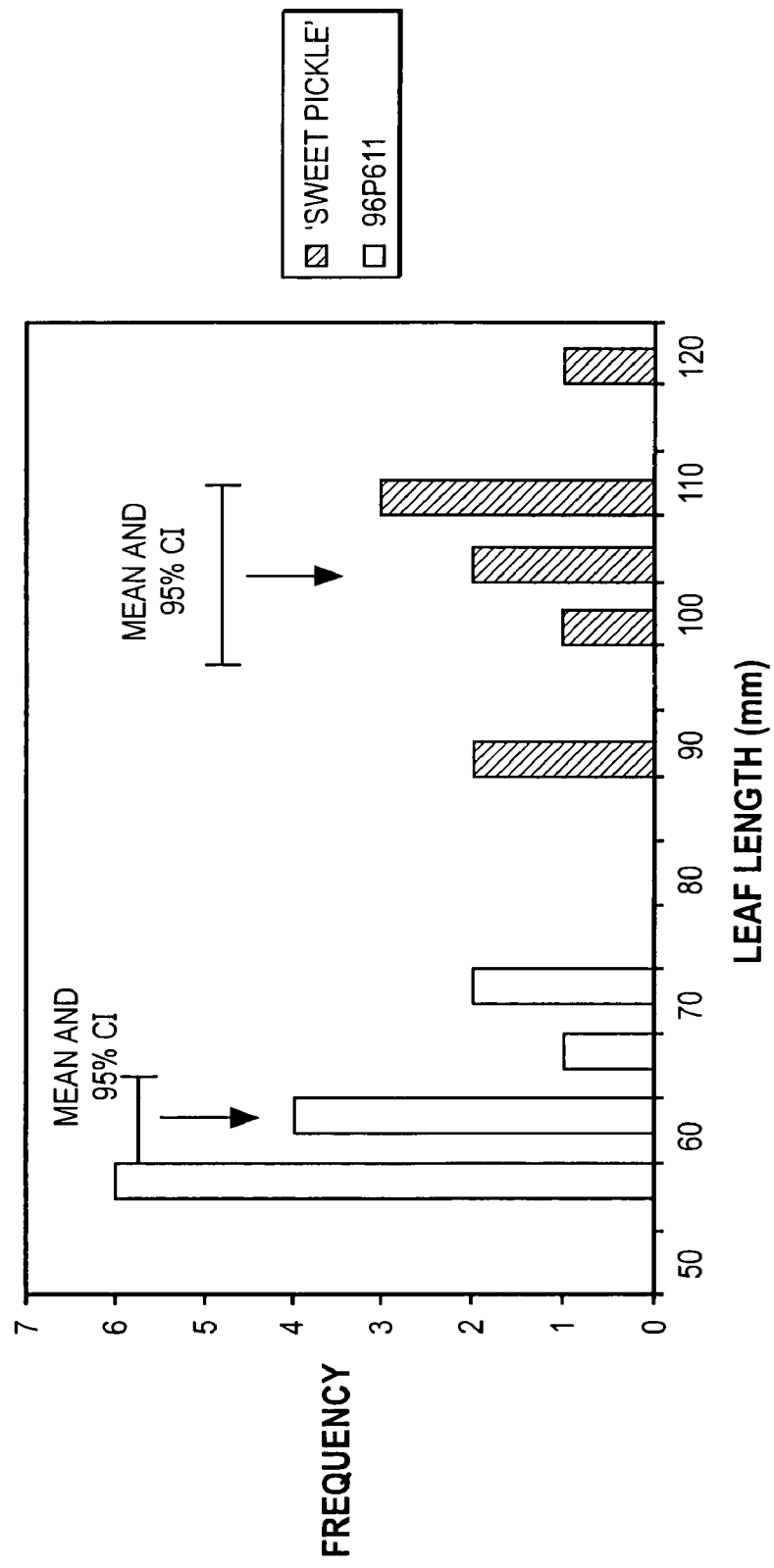
FIG. 6 shows a comparison of the leaf lengths of 'Sweet Pickle' and cultivar 96P611 of the present invention.

Ornamental characteristics of 96P611, hybrid parent of 97P1938 of the present invention, were compared to 'Sweet Pickle' a non-pungent salad pepper marketed by Geo. W. Park Seed Co. Inc., 1 Parkton Avenue, Greenwood, S.C., 29647 using field grown plants from two replicated plots. Samples were evaluated for fruit weight, leaf width and leaf length. ANOVA results determined that differences between replicates were non-significant. Variation within samples from each variety was used to establish confidence intervals. As shown in FIGS. 3–5, cultivar 96P611 possesses the superior ornamental characteristics of smaller fruit weight and leaf size when compared to 'Sweet Pickle'.

Deposit Information

Two thousand five hundred (2500) seeds of a non-pungent ornamental pepper 96P610 have been placed on deposit with the American Type Culture Collection (ATCC), 10801 University Blvd., Manassus, Va., 20110-2209 under Deposit Accession Number 203779 on Feb. 17, 1999. This deposit was made in compliance with the Budapest Treaty requirements that the duration of the deposit should be for thirty (30) years from the date of deposit or for five (5) years after the last request for the deposit at the depository or for the enforceable life of a U.S. patent that matures from this application, whichever is longer. These ornamental pepper seeds will be replenished should it become non-viable at the depository.

Two thousand five hundred (2500) seeds of non-pungent ornamental pepper 96P611 have been placed on deposit with the American Type Culture Collection (ATCC), 10801 University Blvd., Manassus, Va., 20110-2209 under Deposit Accession Number PTA-5689 on Dec. 8, 2003. This deposit was made in compliance with the Budapest Treaty requirements that the duration of the deposit should be thirty (30) years from the date of deposit or for five (5) years after the last request for the deposit at the depository or for the enforceable life of a U.S. patent that matures from this application, whichever is longer. These ornamental pepper seeds will be replenished should it become non-viable at the depository.

Two thousand five hundred (2500) seeds of non-pungent ornamental pepper 97P1938 have been placed on deposit with the American Type Culture Collection (ATCC), 10801 University Blvd., Manassus, Va., 20110-2209 under Deposit Accession Number PTA-5749 on Jan. 7, 2004. This deposit was made in compliance with the Budapest Treaty requirements that the duration of the deposit should be thirty (30) years from the date of deposit or for five (5) years after the last request for the deposit at the depository or for the enforceable life of a U.S. patent that matures from this application, whichever is longer. These ornamental pepper seeds will be replenished should it become non-viable at the depository.

What is claimed is:

1. A *Capsicum annuum* seed designated as 96P610, a sample of which is deposited under ATCC Accession Number 203779.

2. A *Capsicum annuum* plant or a part thereof grown from the seed of claim 1.

3. Pollen of the plant of claim 2.

4. An ovule of the plant of claim 2.

5. A tissue culture comprising regenerable cells produced from the plant of claim 2.

6. A cutting of the plant of claim 2.

7. A *Capsicum annuum* plant, or a part thereof, regenerated from the tissue culture of claim 5 having all the morphological and physiological characteristics of a *Capsicum annuum* plant 96P610, representative seed of which has been deposited under ATCC accession number 203779.

8. A *Capsicum annuum* seed designated as 96P611, a sample of which is deposited under ATCC Accession Number PTA-5689.

9. A *Capsicum annuum* plant or a part thereof grown from the seed of claim 8.

10. Pollen of the plant of claim 9.

11. An ovule of the plant of claim 9.

12. A tissue culture comprising regenerable cells produced from the plant of claim 9.

13. A cutting of the plant of claim 9.

14. A *Capsicum annuum* plant, or a part thereof, regenerated from the tissue culture of claim 12 having all the morphological and physiological characteristics of a *Capsicum annuum* plant 96P611, representative seed of which has been deposited under ATCC accession number PTA-5689.

15. A *Capsicum annuum* seed designated as 97P1938, a sample of which is deposited under ATCC Accession Number PTA-5739.

16. A *Capsicum annuum* plant or a part thereof grown from the seed of claim 15.

17. Pollen of the plant of claim 16.

18. An ovule of the plant of claim 16.

19. A tissue culture comprising regenerable cells produced from the plant of claim 16.

20. A cutting of the plant of claim 16.

21. A *Capsicum annuum* plant, or a part thereof, regenerated from the tissue culture of claim 19 having all the morphological and physiological characteristics of a *Capsicum annuum* plant 97P1938, representative seed of which has been deposited under ATCC accession number PTA-5749.

* * * * *

UNITED STATES PATENT AND TRADEMARK OFFICE
CERTIFICATE OF CORRECTION

PATENT NO. : 7,087,819 B2
APPLICATION NO. : 09/564153
DATED : August 8, 2006
INVENTOR(S) : Marlin Edwards Page 1 of 1

It is certified that error appears in the above-identified patent and that said Letters Patent is hereby corrected as shown below:

Column 9, Claim 15, line 3, remove "PTA-5739" and replace with -- PTA-5749 --.

Signed and Sealed this

Thirtieth Day of June, 2009

JOHN DOLL
*Acting Director of the United States Patent and Trademark Office*